(12) United States Patent
Dixit et al.

(10) Patent No.: US 9,789,321 B2
(45) Date of Patent: Oct. 17, 2017

(54) COUPLINGS FOR IMPLANTED LEADS AND EXTERNAL STIMULATORS, AND ASSOCIATED SYSTEMS AND METHODS

(71) Applicant: Nevro Corporation, Menlo Park, CA (US)

(72) Inventors: Apratim N. Dixit, Menlo Park, CA (US); Vivek Sharma, San Ramon, CA (US); Andre B. Walker, Monte Sereno, CA (US)

(73) Assignee: Nevro Corp., Redwood City, CA (US)

( * ) Notice: Subject to any disclaimer, the term of this patent is extended or adjusted under 35 U.S.C. 154(b) by 0 days.

(21) Appl. No.: 14/678,785

(22) Filed: Apr. 3, 2015

(65) Prior Publication Data

US 2016/0287881 A1    Oct. 6, 2016

(51) Int. Cl.
| | |
|---|---|
| *A61N 1/00* | (2006.01) |
| *A61N 1/375* | (2006.01) |
| *A61N 1/05* | (2006.01) |
| *H01R 13/629* | (2006.01) |
| *H01R 35/04* | (2006.01) |
| *H01R 24/58* | (2011.01) |
| *H01R 31/06* | (2006.01) |

(52) U.S. Cl.
CPC ......... *A61N 1/3752* (2013.01); *A61N 1/0551* (2013.01); *H01R 13/62905* (2013.01); *H01R 35/04* (2013.01); *H01R 24/58* (2013.01); *H01R 31/065* (2013.01); *H01R 2201/12* (2013.01)

(58) Field of Classification Search
CPC .......................... A61N 1/3752; A61N 1/0551
USPC ................................ 607/2, 46, 117
See application file for complete search history.

(56) References Cited

U.S. PATENT DOCUMENTS

| | | |
|---|---|---|
| 4,211,462 A | 7/1980 | Wolfthal |
| 4,466,690 A | 8/1984 | Osypka |
| 4,498,482 A | 2/1985 | Williams |
| 4,573,448 A | 3/1986 | Kambin |
| 4,683,895 A | 8/1987 | Pohndorf |
| 4,764,132 A | 8/1988 | Stutz, Jr. |
| 4,796,642 A | 1/1989 | Harris |
| 4,898,173 A | 2/1990 | Daglow et al. |
| 4,934,367 A | 6/1990 | Daglow et al. |

(Continued)

FOREIGN PATENT DOCUMENTS

| | | |
|---|---|---|
| CN | 101920065 A | 12/2010 |
| EP | 0158316 A2 | 10/1985 |

(Continued)

*Primary Examiner* — Nadia A Mahmood
(74) *Attorney, Agent, or Firm* — Perkins Coie LLP

(57) ABSTRACT

Couplings for implanted leads and external stimulators, and associated systems and methods are disclosed. A connector in accordance with a particular embodiment includes a first housing portion and a second housing portion pivotably connected to each other. The first housing portion has an elongated fixed stop opening. The second housing portion has a stop element and a plurality of connector contacts positioned to electrically contact a plurality of connection contacts of a spinal cord stimulation lead. The first and second housing portions are pivotably connected to each other to move between a partially-opened position in which the stop element is in a first location in the elongated fixed stop opening, and a closed position in which the stop element has a second location in the elongated fixed stop opening.

24 Claims, 7 Drawing Sheets

(56) References Cited

U.S. PATENT DOCUMENTS

| | | |
|---|---|---|
| 5,042,486 A | 8/1991 | Pfeiler et al. |
| 5,052,375 A | 10/1991 | Stark et al. |
| 5,070,605 A | 12/1991 | Daglow et al. |
| 5,072,458 A | 12/1991 | Suzuki |
| 5,211,165 A | 5/1993 | Dumoulin et al. |
| 5,241,957 A | 9/1993 | Camps et al. |
| 5,257,636 A | 11/1993 | White |
| 5,261,395 A | 11/1993 | Oleen et al. |
| 5,325,873 A | 7/1994 | Hirschi et al. |
| 5,354,326 A | 10/1994 | Comben et al. |
| 5,375,596 A | 12/1994 | Twiss et al. |
| 5,425,367 A | 6/1995 | Shapiro et al. |
| 5,557,210 A | 9/1996 | Cappa et al. |
| 5,560,358 A | 10/1996 | Arnold et al. |
| 5,727,553 A | 3/1998 | Saad |
| 5,730,628 A | 3/1998 | Hawkins |
| 5,848,126 A | 12/1998 | Fujita et al. |
| 5,931,861 A | 8/1999 | Werner et al. |
| 6,039,685 A | 3/2000 | Bushek |
| 6,106,460 A | 8/2000 | Panescu et al. |
| 6,192,278 B1 | 2/2001 | Werner |
| 6,263,230 B1 | 7/2001 | Haynor et al. |
| 6,325,778 B1 | 12/2001 | Zadno-Azizi et al. |
| 6,397,108 B1 | 5/2002 | Camps et al. |
| 6,477,427 B1 | 11/2002 | Stolz et al. |
| 6,516,807 B1 | 2/2003 | Panescu et al. |
| 6,671,534 B2 | 12/2003 | Putz |
| 6,875,571 B2 | 4/2005 | Crabtree et al. |
| 7,299,095 B1 | 11/2007 | Barlow et al. |
| 7,383,090 B2 | 6/2008 | O'Brien et al. |
| 7,421,297 B2 | 9/2008 | Giftakis et al. |
| 7,425,142 B1 | 9/2008 | Putz |
| 7,702,379 B2 | 4/2010 | Avinash et al. |
| 7,810,996 B1 | 10/2010 | Giphart et al. |
| 7,881,806 B2 | 2/2011 | Horrigan et al. |
| 7,996,055 B2 | 8/2011 | Hauck et al. |
| 8,036,756 B2 | 10/2011 | Swoyer et al. |
| 8,078,280 B2 | 12/2011 | Sage |
| 8,197,494 B2 | 6/2012 | Jaggi et al. |
| 8,494,652 B2 | 7/2013 | Cantlon et al. |
| 8,996,128 B2 | 3/2015 | Parker et al. |
| 2002/0052640 A1 | 5/2002 | Bigus et al. |
| 2002/0173718 A1 | 11/2002 | Frisch et al. |
| 2003/0062048 A1 | 4/2003 | Gradon et al. |
| 2003/0114752 A1 | 6/2003 | Henderson et al. |
| 2003/0120150 A1 | 6/2003 | Govari |
| 2003/0136418 A1 | 7/2003 | Behm |
| 2003/0228805 A1 | 12/2003 | Schwarz |
| 2004/0034392 A1 | 2/2004 | Spadgenske |
| 2004/0087877 A1 | 5/2004 | Besz et al. |
| 2004/0097803 A1 | 5/2004 | Panescu |
| 2004/0176683 A1 | 9/2004 | Whitin et al. |
| 2004/0230268 A1 | 11/2004 | Huff et al. |
| 2005/0049486 A1 | 3/2005 | Urquhart et al. |
| 2005/0049664 A1 | 3/2005 | Harris et al. |
| 2005/0075684 A1 | 4/2005 | Phillips et al. |
| 2005/0228221 A1 | 10/2005 | Hirakawa |
| 2006/0030918 A1 | 2/2006 | Chinn et al. |
| 2006/0148326 A1 | 7/2006 | Putz |
| 2006/0253160 A1 | 11/2006 | Benditt et al. |
| 2007/0191903 A1 | 8/2007 | Bruinstroop |
| 2007/0249901 A1 | 10/2007 | Ohline et al. |
| 2008/0097475 A1 | 4/2008 | Jaggi et al. |
| 2008/0140087 A1 | 6/2008 | Barbagli |
| 2008/0262430 A1 | 10/2008 | Anderson et al. |
| 2008/0275467 A1 | 11/2008 | Liao et al. |
| 2008/0319311 A1 | 12/2008 | Hamadeh |
| 2009/0048638 A1 | 2/2009 | Rey et al. |
| 2009/0069803 A1 | 3/2009 | Starkebaum |
| 2009/0112272 A1 | 4/2009 | Schleicher et al. |
| 2009/0125060 A1 | 5/2009 | Rivard et al. |
| 2009/0132016 A1 | 5/2009 | Putz |
| 2009/0233491 A1 | 9/2009 | Barker et al. |
| 2010/0094116 A1 | 4/2010 | Silverstein |
| 2010/0152538 A1 | 6/2010 | Gleason et al. |
| 2010/0256696 A1 | 10/2010 | Schleicher et al. |
| 2010/0267265 A1 | 10/2010 | Dilmaghanian |
| 2010/0274336 A1 | 10/2010 | Nguyen-Stella et al. |
| 2010/0286551 A1 | 11/2010 | Harlev et al. |
| 2010/0305670 A1 | 12/2010 | Hall et al. |
| 2010/0324414 A1 | 12/2010 | Harlev et al. |
| 2011/0031961 A1 | 2/2011 | Durand et al. |
| 2011/0046617 A1 | 2/2011 | Thompson et al. |
| 2011/0071593 A1* | 3/2011 | Parker .................. A61N 1/0551 607/46 |
| 2011/0071604 A1 | 3/2011 | Wahlstrand et al. |
| 2011/0106052 A1 | 5/2011 | Chiang et al. |
| 2011/0106100 A1 | 5/2011 | Bischoff |
| 2011/0112609 A1 | 5/2011 | Peterson |
| 2011/0144468 A1 | 6/2011 | Boggs et al. |
| 2011/0160568 A1 | 6/2011 | Seeley et al. |
| 2011/0166621 A1 | 7/2011 | Cowan et al. |
| 2011/0167630 A1 | 7/2011 | Heruth et al. |
| 2011/0178573 A1 | 7/2011 | Nguyen-Stella et al. |
| 2011/0184488 A1 | 7/2011 | De Ridder |
| 2011/0202097 A1 | 8/2011 | Bonde et al. |
| 2011/0224682 A1 | 9/2011 | Westlund et al. |
| 2011/0224710 A1 | 9/2011 | Bleich |
| 2011/0230943 A1 | 9/2011 | Johnson et al. |
| 2012/0083709 A1 | 4/2012 | Parker et al. |
| 2012/0083856 A1 | 4/2012 | Thacker et al. |
| 2012/0232626 A1 | 9/2012 | Daglow |
| 2016/0059006 A1* | 3/2016 | Doan .................. A61N 1/0573 607/127 |

FOREIGN PATENT DOCUMENTS

| | | |
|---|---|---|
| WO | WO-9003824 A1 | 4/1990 |
| WO | WO-2009129329 A1 | 10/2009 |

* cited by examiner

COUPLINGS FOR IMPLANTED LEADS AND EXTERNAL STIMULATORS, AND ASSOCIATED SYSTEMS AND METHODS

TECHNICAL FIELD

The present disclosure is directed generally to couplings for implanted leads and external stimulators, and associated systems and methods.

BACKGROUND

Neurological stimulators have been developed to treat pain, movement disorders, functional disorders, spasticity, cancer, cardiac disorders, and various other medical conditions. Implantable neurological stimulation systems generally have an implantable pulse generator and one or more leads that deliver electrical pulses to neurological tissue or muscle tissue. For example, several neurological stimulation systems for spinal cord stimulation (SCS) have cylindrical leads that include a lead body with a circular cross-sectional shape and one or more conductive rings spaced apart from each other at the distal end of the lead body. The conductive rings operate as individual electrodes and, in many cases, the SCS leads are implanted percutaneously through a large needle inserted into the epidural space, with or without the assistance of a stylet.

Once implanted, the pulse generator applies electrical pulses to the electrodes, which in turn modify the function of the patient's nervous system, such as by altering the patient's responsiveness to sensory stimuli and/or altering the patient's motor-circuit output. In pain treatment, the pulse generator applies electrical pulses to the electrodes, which in turn can generate sensations that mask or otherwise alter the patient's sensation of pain. For example, in many cases, patients report a tingling or paresthesia that is perceived as more pleasant and/or less uncomfortable than the underlying pain sensation.

One problem associated with existing stimulation systems and methods is that the practitioner may not initially implant the SCS lead in the optimal position. Accordingly, practitioners typically make small adjustments to the position of the implanted lead while the patient is in the operating room. The practitioner then applies stimulation to the lead via an external stimulator, which is temporarily attached to the lead while the lead still extends out of the patient's body. This process is repeated until the practitioner determines the position of the lead that is expected to produce the best patient result. The patient and practitioner can also use the external stimulator during a post-operative trial period, to optimize the characteristics of the applied signal before an implantable pulse generator is connected to the lead and implanted beneath the patient's skin.

To facilitate the foregoing process of alternately providing stimulation to the patient and moving the implanted portion of the lead, manufacturers have developed cables with releasable connectors. Accordingly, the practitioner can connect the cable to the external stimulator and the lead, apply the stimulation, then disconnect the cable, move the lead, and reconnect the cable with the lead in the new position. As noted above, this process can be repeated, as needed, until the desired lead location is obtained.

One drawback with the foregoing approach is that it may be difficult for the practitioner to repeatedly manipulate the connector that attaches the cable to the lead, while still maintaining control over the position of the lead. Additionally, over-manipulation of the connector may inadvertently break the connector. Another drawback is that the connectors, which are outside the patient's body, may be awkward and/or cumbersome for the patient during the post-operative trial period. Accordingly, there remains a need for improved techniques and systems for releasably connecting implanted patient leads to external stimulation devices.

DETAILED DESCRIPTION

Overview

Figure 1:
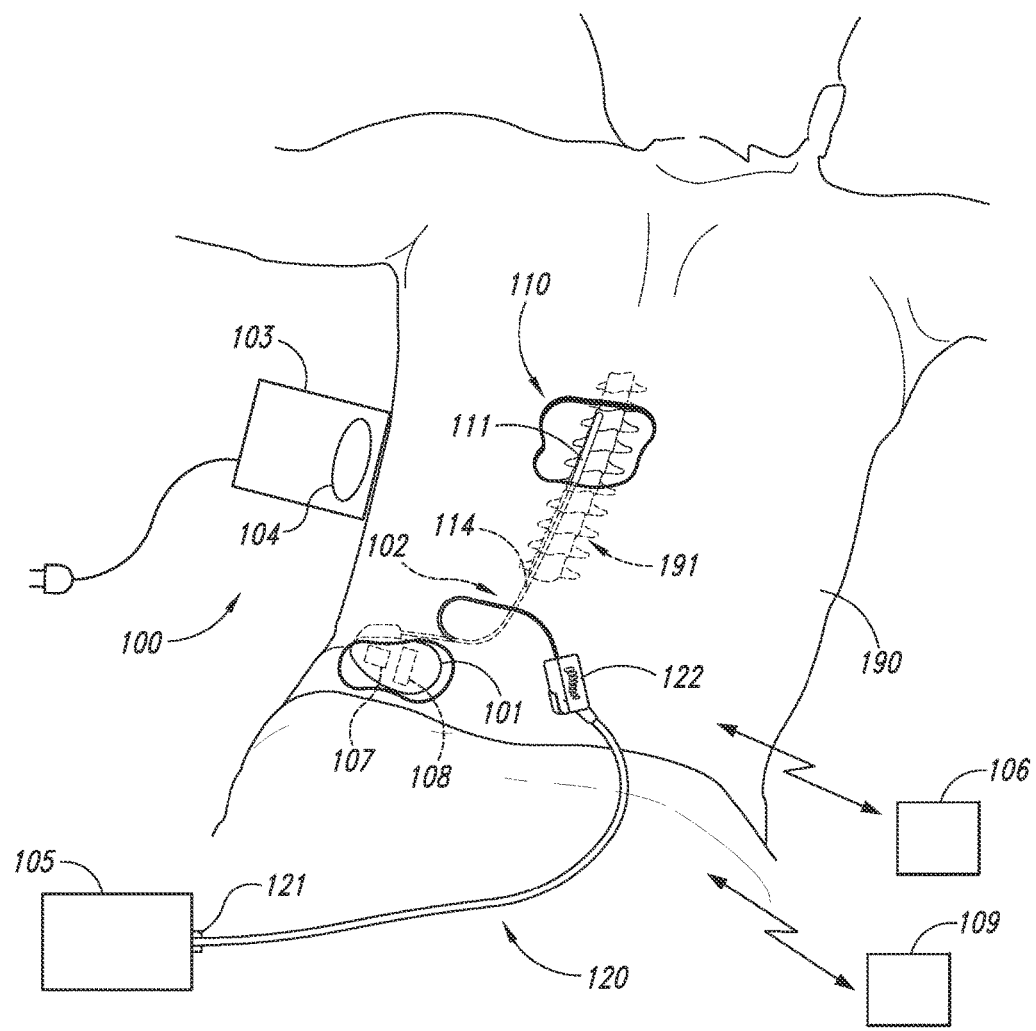
FIG. 1 is a partially schematic illustration of an implantable spinal cord stimulation system positioned at the spine to deliver a therapeutic signal in accordance with an embodiment of the present disclosure.

Aspects of the present disclosure are directed generally to couplings that may be used to connect implanted leads or other implanted signal delivery elements, with external stimulators and/or other devices positioned external to a patient. Several aspects of the disclosure are described in the context of a spinal cord stimulation (SCS) system for purposes of illustration. In other embodiments, the disclosed systems and methods may be used in the context of other patient treatment and/or patient diagnostic systems. Several embodiments of representative systems and methods are described below with reference to FIGS. 1-10. A person skilled in the relevant art will understand, however, that the disclosure may have additional embodiments, and/or that aspects of the disclosure may be practiced without several of the details of the embodiments described below.

A patient treatment system in accordance with a particular embodiment includes a cable assembly that in turn includes an electrical cable having a proximal end and a distal end, with a first connector attached to the cable toward the proximal end, and a second connector attached to the cable toward the distal end. The first connector can include a plurality of first connector contacts positioned to releasably connect to an external patient device, for example, an external stimulator. The second connector can include a first portion and a second portion pivotably connected to the first portion. The first portion can have a slot elongated along a slot axis and positioned to receive an implantable patient signal delivery element axially along the slot axis. The second portion can have a plurality of second connector contacts positioned to releasably, electrically contact the signal delivery element when the signal delivery element is positioned within the slot and the first and second portions are placed in a secured position. The first and second portions are pivotable relative to each other between a closed position and a partially-opened position.

A representative method for operating a patient treatment system can include implanting an implantable signal delivery element in a patient, and positioning a cable proximate to connection contacts of the implantable signal delivery device. The cable can include a proximal end with a first connector having first connector contacts, and a distal end with a second connector having first and second portions. The method can further include sliding the connection contacts of the signal delivery element axially into a slot carried by the second portion of the second connector. The method can still further include pivoting at least one of the first and second portions relative to the other to electrically connect the connection contacts of the signal delivery device with second connector contacts carried by the second portion of the second connector. The first connector can be releasably connected to an external patient device, for example, an external patient stimulator. As will be described further below, aspects of the foregoing systems and associated methods can allow the practitioner to manipulate the cable assembly connectors with only one hand, and/or can improve patient comfort while the cable assembly is connected to an implanted lead or other signal delivery element.

Representative Systems and Methods

FIG. 1 schematically illustrates a representative treatment system 100 for providing relief from chronic pain and/or other conditions, arranged relative to the general anatomy of a patient's spinal cord 191. The system 100 can include a pulse generator 101, which may be implanted subcutaneously within a patient 190 and coupled to a signal delivery element 110. In a representative example, the signal delivery element 110 includes a lead or lead body 111 that carries features or elements for delivering therapy to the patient 190 after implantation. The pulse generator 101 can be connected directly to the lead 111, or it can be coupled to the lead 111 via a communication link 102 (e.g., an extension). Accordingly, the lead 111 can include a terminal section that is releasably connected to an extension at a break 114 (shown schematically in FIG. 1). This allows a single type of terminal section to be used with patients of different body types (e.g., different heights). As used herein, the terms lead and lead body include any of a number of suitable substrates and/or support members that carry devices for providing therapy signals to the patient 190. For example, the lead 111 can include one or more electrodes or electrical contacts that direct electrical signals into the patient's tissue, such as to provide for patient relief. In other embodiments, the signal delivery element 110 can include devices other than a lead body (e.g., a paddle) that also direct electrical signals and/or other types of signals to the patient 190.

The pulse generator 101 can transmit signals to the signal delivery element 110 that up-regulate (e.g., stimulate or excite) and/or down-regulate (e.g., block or suppress) target nerves. As used herein, and unless otherwise noted, the terms "stimulate," "stimulation," and more generally, "modulation," refer to signals that have either type of effect on the target nerves. The pulse generator 101 can include a machine-readable (e.g., computer-readable) medium containing instructions for generating and transmitting suitable therapy signals. The pulse generator 101 and/or other elements of the system 100 can include one or more processors 107, memories 108 and/or input/output devices. Accordingly, the process of providing stimulation signals and executing other associated functions can be performed by computer-executable instructions contained on computer-readable media, e.g., at the processor(s) 107 and/or memory(s) 108. The pulse generator 101 can include multiple portions, elements, and/or subsystems (e.g., for directing signals in accordance with multiple signal delivery parameters), housed in a single housing, as shown in FIG. 1, or in multiple housings.

In some embodiments, the pulse generator 101 can obtain power to generate the therapy signals from an external power source 103. The external power source 103 can transmit power to the implanted pulse generator 101 using electromagnetic induction (e.g., RF signals). For example, the external power source 103 can include an external coil 104 that communicates with a corresponding internal coil (not shown) within the implantable pulse generator 101. The external power source 103 can be portable for ease of use.

In another embodiment, the pulse generator 101 can obtain the power to generate therapy signals from an internal power source, in addition to or in lieu of the external power source 103. For example, the implanted pulse generator 101 can include a non-rechargeable battery or a rechargeable battery to provide such power. When the internal power source includes a rechargeable battery, the external power source 103 can be used to recharge the battery. The external power source 103 can in turn be recharged from a suitable power source (e.g., conventional wall power).

In many cases, an external programmer 105 (e.g., a trial stimulator) is coupled to the signal delivery element 110 during an initial implant procedure, prior to implanting the pulse generator 101. For example, a practitioner (e.g., a physician and/or a company representative) can use the external programmer 105 to vary the signal delivery parameters provided to the signal delivery element 110 in real time, and select optimal or particularly efficacious parameters. These parameters can include the position of the signal delivery element 110, as well as the characteristics of the electrical signals provided to the signal delivery element 110. In a typical process, the practitioner uses a cable assembly 120 to temporarily connect the external programmer 105 to the signal delivery device 110. The cable assembly 120 can accordingly include a first connector 121 that is releasably connected to the external programmer 105, and a second connector 122 that is releasably connected to the signal delivery element 110. The practitioner can test the efficacy of the signal delivery element 110 in an initial position. The practitioner can then disconnect the cable assembly 120, reposition the signal delivery element 110, and reapply the electrical stimulation. This process can be performed iteratively until the practitioner obtains the desired position for the signal delivery device 110. Optionally, the practitioner may move the partially implanted signal delivery element 110 without disconnecting the cable assembly 120. In either embodiment, the practitioner will connect and disconnect the cable assembly 120 at least once during the process. Further details of features that facilitate this process are described below with reference to FIGS. 3-10.

After the position of the signal delivery element 110 and appropriate signal delivery parameters are established using the external programmer 105, the patient 190 can receive therapy via signals generated by the external programmer 105, generally for a limited period of time. In a representative application, the patient 190 receives such therapy for a one-week trial period. During this time, the patient wears the cable assembly 120 and the external programmer 105 outside the body. Assuming the trial therapy is effective or shows the promise of being effective, the practitioner then replaces the external programmer 105 with the implanted pulse generator 101, and programs the pulse generator 101 with parameters selected based on the experience gained during the trial period. Optionally, the practitioner can also replace the signal delivery element 110. Once the implantable pulse generator 101 has been positioned within the patient 190, the signal delivery parameters provided by the pulse generator 101 can still be updated remotely via a wireless physician's programmer (e.g., a physician's remote) 109 and/or a wireless patient programmer 106 (e.g., a patient remote). Generally, the patient 190 has control over fewer parameters than does the practitioner. For example, the capability of the patient programmer 106 may be limited to starting and/or stopping the pulse generator 101, and/or adjusting stimulation amplitude.

Figure 2:
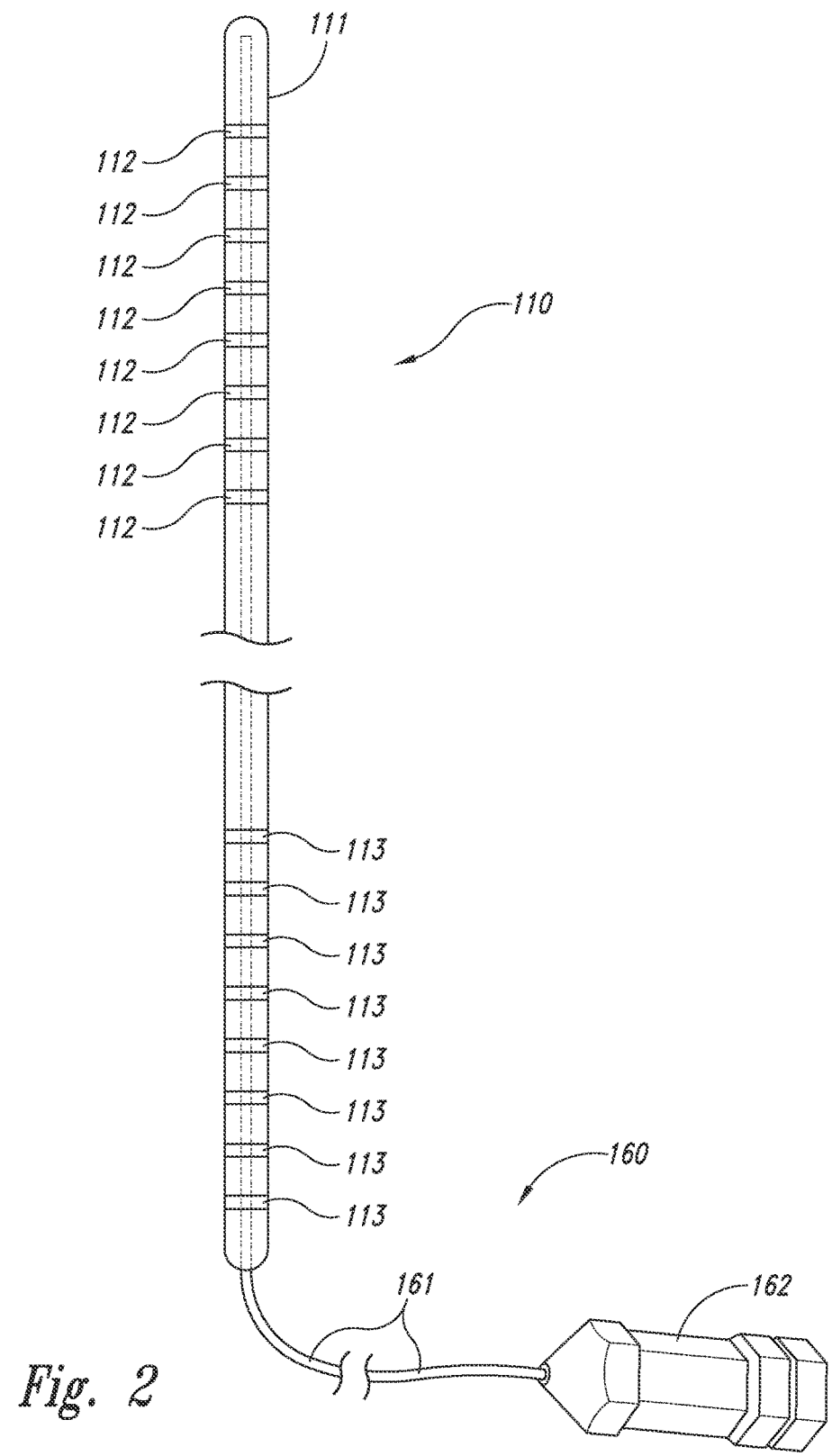
FIG. 2 is a partially schematic illustration of a lead having stimulation contacts and externally positioned connector contacts, suitable for providing stimulation in accordance with representative methods of present disclosure.

FIG. 2 is a partially schematic illustration of a representative signal delivery device 110 that includes a lead 111 having a plurality of stimulation contacts 112 toward the distal end that are implanted within the patient. The lead 111 includes internal wires that extend between the stimulation contacts 112 at the distal end and connection contacts 113 positioned at the proximal end. During the trial period, the connection contacts 113 extend outside the patient's body and are connected to an external stimulator. After the trial period is complete, the connection contacts 113 are connected to the implanted pulse generator 101 (FIG. 1). During implantation, a stylet 160 or other delivery device is temporarily connected to the lead 111 to support the lead 111 as it is positioned within the patient. Accordingly, the stylet 160 can include a shaft 161 and a handle 162. The shaft 161 is generally flexible, but more rigid than the lead 111 to allow the practitioner to insert the lead 111 and control its position during implantation.

Figure 3:
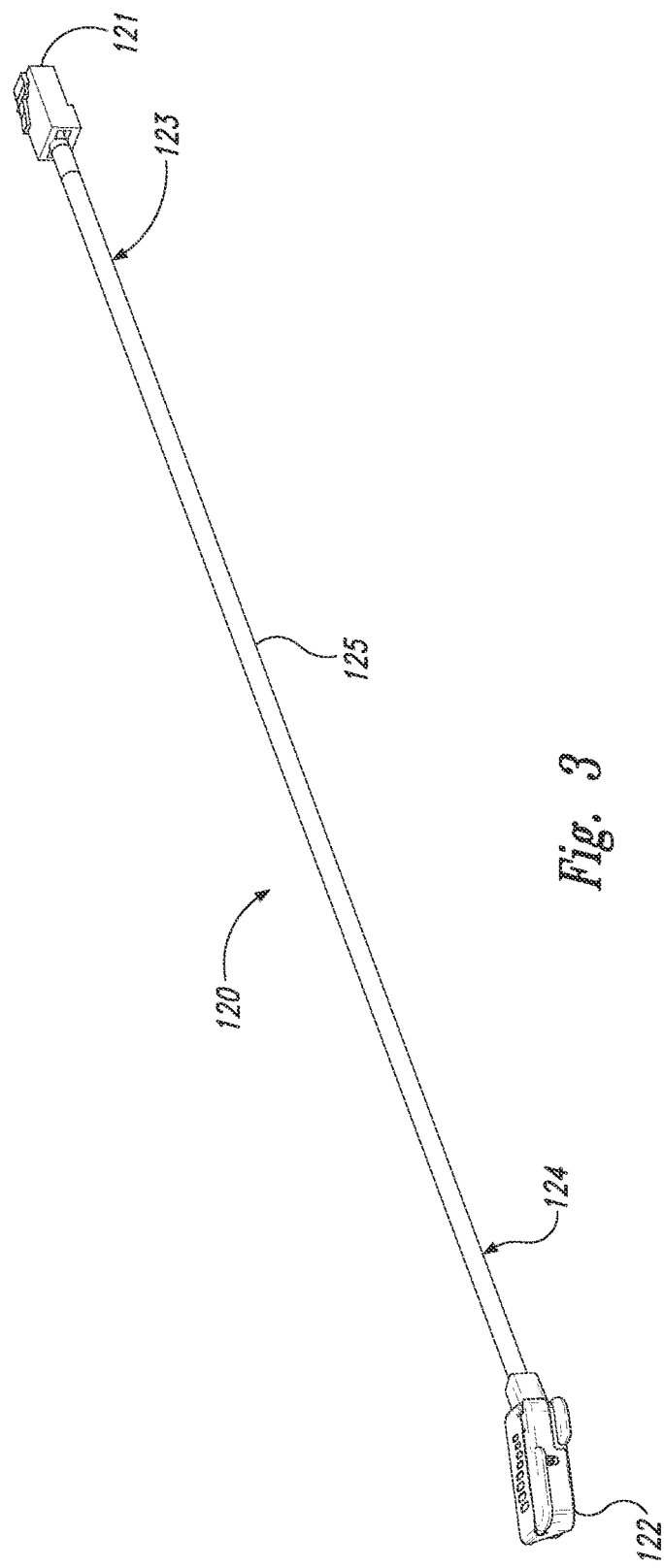
FIG. 3 is a partially schematic, isometric illustration of a cable assembly suitable for releasably coupling a patient lead or other signal delivery element to an external stimulator or other device in accordance with an embodiment of the disclosure.

FIG. 3 is a partially schematic, isometric illustration of a cable assembly 120 that can be releasably connected to the signal delivery element 110 shown in FIG. 2. The cable assembly 120 includes a cable 125 carrying a plurality of electrical conductors 126. A first connector 121 is positioned toward a proximal end 123. A second connector 122 is connected to the cable 125 toward a distal end 124 and includes second connector contacts 153 (FIG. 4), also connected to the electrical conductors 126.

Figure 4:
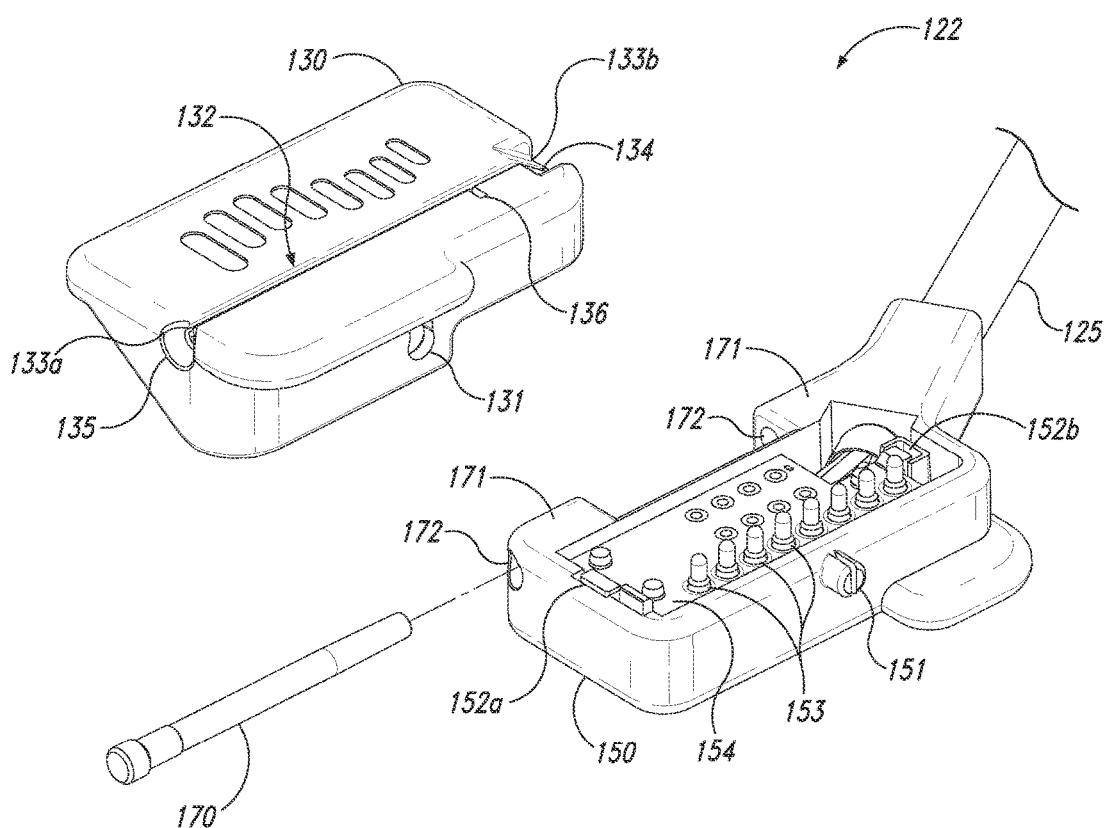
FIG. 4 is an exploded, partially schematic illustration of a connector configured in accordance with an embodiment of the disclosure.

FIG. 4 is a partially schematic, partially exploded isometric illustration of the cable 125 and the second connector 122. The bulk of the second connector 122 can be formed from ABS or another suitable biocompatible plastic or other material. In a particular aspect of this embodiment, the second connector 122 includes a first portion, e.g., a first housing portion 130 pivotably connected to a second portion, e.g., a second housing portion 150, via a hinge pin 170. Accordingly, at least one of the first housing portion 130 and the second housing portion 150 can be pivoted relative to the other between a closed position and a partially-opened position. The second connector 122 can have a corresponding closed configuration and partially-opened configuration, respectively.

The first housing portion 130 includes a stop opening 131 that interfaces with a stop element 151 (carried by the second housing portion 150) to control the pivoting motion of the first and second housing portions 130, 150. The first housing portion 130 also includes a slot 132 elongated along a slot axis 133. The slot 132 can include a first opening 134a positioned toward one end of the slot axis 133, a second opening 134b positioned toward the opposite end of the slot axis 133, and a third opening 134c extending along the slot axis 133 between the first opening 134a and the second opening 134b. The slot 132 is positioned to receive a lead or other signal delivery device, and an associated stylet. Accordingly, the first opening 134a can have a first width sized to receive the lead, the second opening 134b can have a smaller second width sized to receive the stylet shaft, and the third opening 134c can have a third width, also sized to receive the stylet shaft. As further shown in FIG. 4, the slot 132 can include a funnel surface 137 at the first opening 134a to facilitate sliding a lead into the slot 132 along the slot axis 133. A ramp surface 138 at the second opening 134b can facilitate movement of the stylet handle 162 (FIG. 2) relative to the slot 132.

An alignment indicator 136 provides the practitioner with visual confirmation that the lead is properly aligned. The first housing portion 130 can include a first tab 135 and the second housing portion 150 can include a second tab 155, both of which facilitate pivoting the two housing portions relative to each other. For example, the two tabs 135, 155 can be offset from each other in a direction generally parallel to the slot axis 133 to operate in a manner similar to that of a change purse.

As further shown in FIG. 4, the second housing portion 150 includes two outer hinge elements 171, each having second pin apertures 172 that slidably receive a corresponding hinge pin 170. The hinge pin 170 also passes through a corresponding inner hinge element carried by the first housing portion 130. The second housing portion 150 can carry a support member 154 that in turn carries second connector contacts 153. The second connector contacts 153 are electrically connected to the electrical conductors 126 (FIG. 3) carried by the cable 125. The second connector contacts 153 project upwardly toward the first housing portion 130 so as to releasably engage with a lead placed in the slot 132 of the first housing portion 130.

Figure 5:
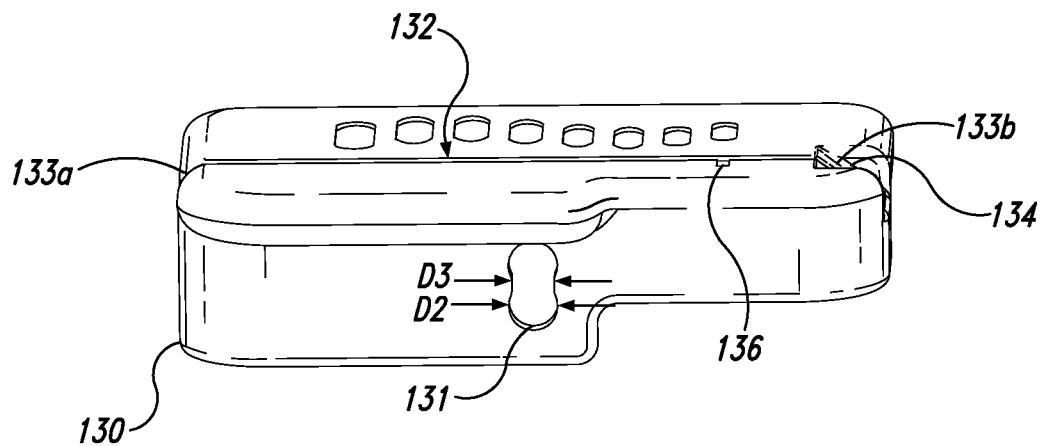
FIG. 5 is a partially schematic, isometric view of a first housing portion of an embodiment of the connector shown in FIG. 4.

FIG. 5 is a partially schematic, isometric view of the first housing portion 130 in accordance with an embodiment of the second connector 122 shown in FIG. 4. As shown in FIG. 5, the first housing portion 130 includes a stop opening 131. In a particular embodiment, the stop opening 131 includes an elongated slot with each end of the stop opening 131 wider than the middle portion, which has pinched or narrowed sides. For example, in one embodiment, the stop opening 131 may be dumbbell-shaped, and can be hourglass-shaped in another embodiment.

Figure 6:
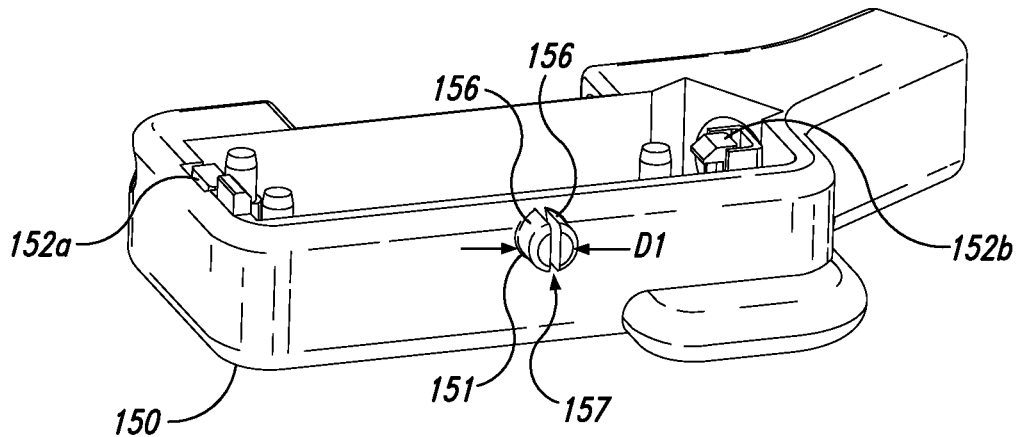
FIG. 6 is a partially schematic, isometric view of a second housing portion of an embodiment of the connector shown in FIG. 4.

FIG. 6 is a partially schematic, isometric view of the second housing portion 150 in accordance with an embodiment of the second connector 122 shown in FIG. 4. The second housing portion 150 can include snap-fit latches 152a, 152b for securing the support member 154 shown in FIG. 4. As is also shown in FIG. 6, the second housing portion 150 includes a stop element 151. The stop element 151 is sized to fit securely in each end of the stop opening 131 in the first housing portion 130. In a particular embodiment, the stop element 151 includes two (or more) prongs 156 having proximal ends that are fixed relative to each other (e.g., at the second housing portion 150), and distal ends that are separated by a gap 157 so as to move toward and away from each other. The prongs 156 can be made of a resilient material so as to maintain the relative positions shown in FIG. 6 in the absence of an external force.

Referring to FIGS. 5 and 6 together, the stop element 151 can have an outer dimension of D1 (FIG. 6), and the ends of the stop opening 131 (FIG. 5) can have an inner dimension of D2. D2 is less than D1 (e.g., 0.95 D1) so that the stop element 151 is snugly received at either end of the stop opening 131. The middle portion of the stop opening can have a still smaller inner dimension D3 (e.g., 0.8 D1) to resist relative motion between the first housing portion 130 (which carries the stop opening 131) and the second housing portion 150 (which carries the stop element 151).

Figure 7A:
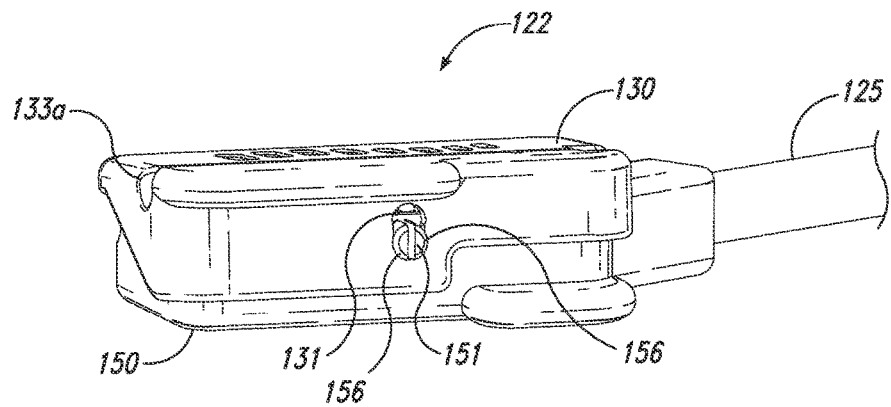
FIGS. 7A and 7B are partially schematic, isometric views of an embodiment of the connector shown in a partially-opened positioned and a closed position, respectively, in accordance with an embodiment of the disclosure.
Figure 7B:
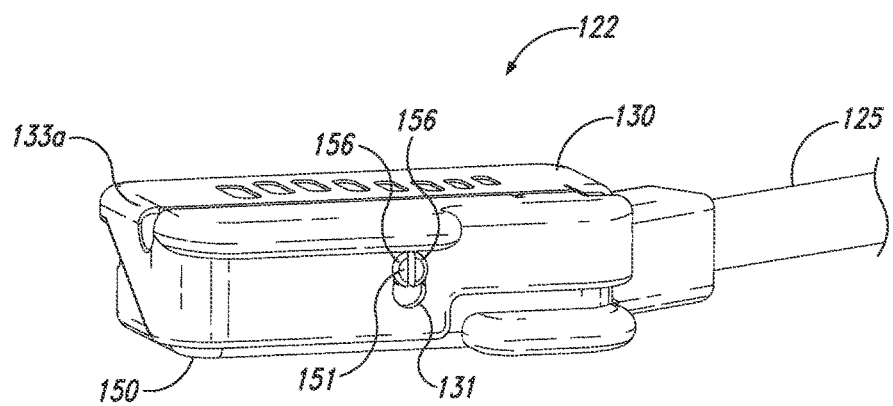

FIGS. 7A and 7B are partially schematic, isometric views of an embodiment of the second connector shown in a partially-opened positioned (FIG. 7A) and a closed position (FIG. 7B) in accordance with an embodiment of the disclosure. FIG. 7A illustrates the second connector 122 in the partially-opened position in which the stop element 151 is in a first location in the stop opening 131. FIG. 7B illustrates the second connector 122 in the closed position in which the stop element 151 is in a second location in the stop opening 131. The location of the stop element 151 relative to the stop opening 131 can change as the second connector 122 moves from the first, partially-opened position to the second, closed position. The change in relative location results from the relative movement of the first housing portion 130 and the second housing portion 150, regardless of which housing portion moves relative to the other. As the housing portion or portions move, the prongs 156 move toward each other to fit through the narrow portion of the stop opening 131. When the prongs 156 reach either end of the stop opening 131, they move apart from each other to hold the second connector 122 in the desired position (closed or partially open) until the practitioner deliberately changes the position. Accordingly, the stop element 151 resists relative movement of the housing portions 130, 150 so that the second connector 122 is less likely to be opened or closed inadvertently.

Figure 8A:
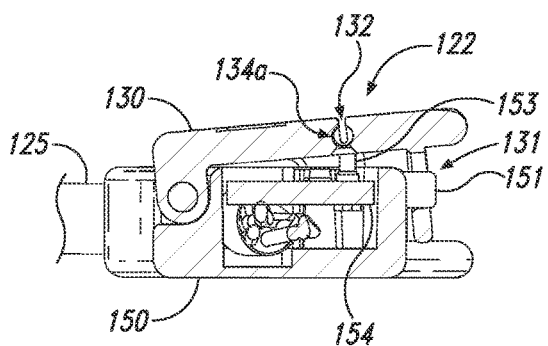
FIGS. 8A and 8B illustrate side views of a connector shown in a partially-opened position and a closed position, respectively, in accordance with an embodiment of the disclosure.
Figure 8B:
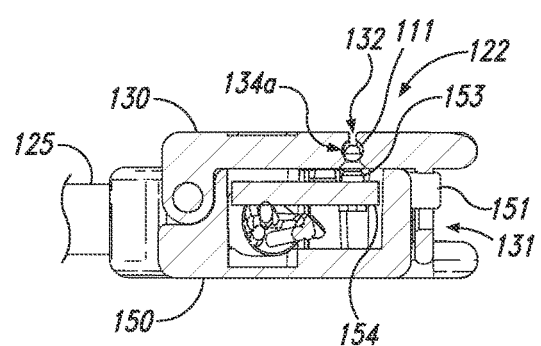

FIGS. 8A and 8B are cross-sectional illustrations of the second connector 122 shown in the partially-opened position (FIG. 8A) and the closed position (FIG. 8B). In FIG. 8A, the first housing portion 130 is pivoted away from the second housing portion 150 to the partially-opened position. A lead 111 is inserted into the first opening 134a, but does not yet contact the second connector contacts 153 carried by the support member 154 of the second housing portion 150. In this position, the first housing portion 130 is prevented from over-rotating relative to the second housing portion 150 because the stop element 151 is received at one end of the stop opening 131 of the first housing portion 130. In a particular embodiment, the stop opening 131 can be sized to prevent the first and second housing portions 130, 150 from rotating away from each other by an angle between 0.5° and 45°, inclusive. In other embodiments, the amount of rotation can be less, for example, between 3° and 15°, inclusive, between 5° and 8°, inclusive, or between 6.5° and 7°, inclusive. The particular angular value can be selected so that the connection contacts of the lead just disengage from the second connector contacts 153 when the second connector 122 is in the partially-opened position. In any of these embodiments, it is expected that limiting the relative rotation of the two housing portions 130, 150 can facilitate the user's ability to secure and/or unsecure the second connector 122, for example, by facilitating single handed operation of the second connector 122.

FIG. 8B illustrates the second connector 122 in the closed position, in which the stop element 151 is in the second location in the stop opening 131. In this position, the first and second housing portions 130, 150 have been pivoted toward each other, so that the lead 111 engages with the second connector contacts 153. At least a portion of each second connector contact 153 can be received in the slot 132 so that the second connector contacts 153 do not interfere with moving the housing portions 130, 150 toward each other to the secured position. In this position, the second connector 122 can remain in the secured position until positively acted upon by the practitioner.

Figure 9:
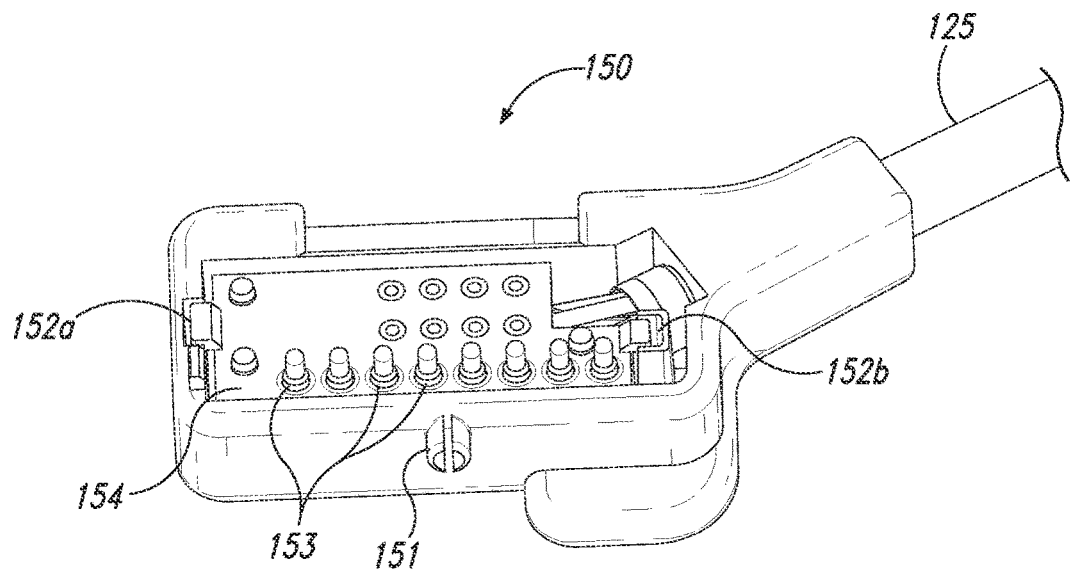
FIG. 9 is a downwardly looking oblique view of an embodiment of a second housing portion of an embodiment of the connector.

FIG. 9 illustrates an embodiment of the second housing portion 150. The snap-fit latches 152a, 152b receive and secure the support member 154 within the second housing 150.

Figure 10:
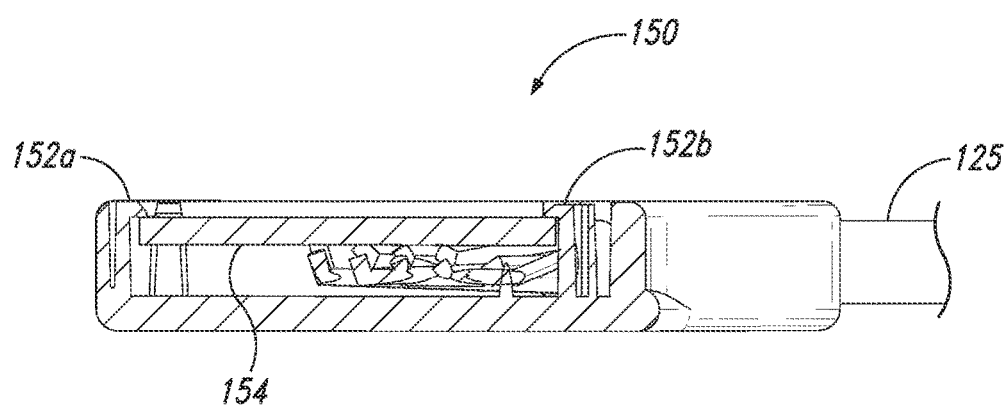
FIG. 10 illustrates a side view of an embodiment of the connector.

FIG. 10 is a cross-sectional side view of the second housing portion 150. As shown in FIG. 10, the support member 154 is secured into the second housing portion by snap-fit latches 152a, 152b.

One feature of at least some of the foregoing embodiments described above with reference to FIGS. 1-10 is that the lead 111 or other signal delivery element 110 can be introduced into the second connector 122 by sliding it axially into and along the slot 132, without at the same time engaging the connection contacts 113 with the second connector contacts 153. As a result, the lead 111 can be moved into the slot 132 easily, with low frictional resistance, and with a reduced likelihood for dislodging or otherwise moving the lead 111 relative to the patient. When the practitioner does engage the connection contacts 113 with the second connector contacts 153, the practitioner can do so with only one hand, allowing the practitioner to hold the lead 111 in place relative to the patient with the other hand. For example, the practitioner's hand can provide both the moving force and the reaction force imparted to the second connector 122, which reduces the likelihood for the second connector 122 to slip out of the practitioner's grasp.

Another feature of at least some of the foregoing embodiments is that the angle between the two housing portions 130, 150 is relatively small when the second connector 122 is in the partially-opened configuration. For example, the angle can be between 0.5° and 45° in a particular embodiment, between 3° and 15° in another particular embodiment, between 5° and 8° in a further particular embodiment, and between 6.5° and 7° in still a further particular embodiment. Accordingly, the amount of hand movement required to secure and/or unsecure the second connector 122 is relatively small, which decreases the likelihood that the practitioner will fumble with the second connector 122.

Still another feature of at least some of the foregoing embodiments is that the second connector 122 has a relatively small footprint (e.g., projected area, generally normal to the major surfaces of the first or second housing portions 130, 150). An expected advantage of this feature is that the small size makes the second connector 122 easier to manipulate. Another expected advantage of this feature is that the second connector will be less bulky and therefore more comfortable for the patient to wear during the trial period.

From the foregoing, it will be appreciated that specific embodiments of the disclosure have been described herein for purposes of illustration, but that various modifications may be made without deviating from the disclosure. For example, in other embodiments, the second connector can include other arrangements for securing one housing portion relative to the other, and/or for halting the axial movement of the lead or other signal delivery element positioned in the second connector. The stop element 151 can, in some embodiments, have a configuration different than the multi-pronged configuration shown in the figures. The relative positions of the stop element and the stop slot can be reversed, with the stop element carried by the first housing portion, and the stop slot carried by the second housing portion. In yet further embodiments, the practitioner can leave the second connector attached to the implanted signal delivery element while the signal delivery element is repositioned, rather than disconnecting and reconnecting the connector with each new signal delivery element position.

Certain aspects of the disclosure described in the context of particular embodiments may be combined or eliminated in other embodiments. For example, in certain embodiments, the signal delivery element can have features different than those shown in FIG. 2, and/or can be supported by a device other than a stylet. Further, while advantages associated with certain embodiments have been described in the context of those embodiments, other embodiments may also exhibit such advantages and not all embodiments need necessarily exhibit such advantages to fall within the scope of the present disclosure. Accordingly, the disclosure can encompass other embodiments not expressly described or shown herein.

We claim:

1. A cable assembly for a spinal cord stimulation system, the cable assembly comprising:
   an electrical cable having a proximal end and a distal end;
   a first connector attached to the proximal end of the cable, the first connector having a plurality of first connector contacts positioned to connect to a spinal cord stimulator; and
   a second connector attached to the distal end of the cable, the second connector including:
      a first housing portion having a stop opening extending therethrough, and a longitudinally extending slot that is configured to slidably receive a portion of a spinal cord stimulation lead; and
      a second housing portion having a stop element received in the stop opening and moveable within the stop opening, a plurality of second connector contacts positioned to electrically contact a plurality of connection contacts of the lead, and a plurality of snap-fit latches to securely carry a surface having second connector contacts,
      wherein the first and second housing portions are pivotably connected to each other to move between a partially-opened position, in which the stop element is in a first location within the stop opening, and a closed position in which the stop element is in a second location within the stop opening.

2. The system of claim 1, wherein in the partially-opened position, the connection contacts of the lead disengage from the second connector contacts.

3. The system of claim 1, wherein in the closed position, the connection contacts of the lead engage with the second connector contacts.

4. The system of claim 1, wherein in the partially-opened position, a maximum opening angle between the first and second housing portions of the second connector is between 3° and 15°, inclusive.

5. The system of claim 1, wherein in the partially-opened position, a maximum opening angle between the first and second housing portions of the second connector is between 5° and 8°, inclusive.

6. The system of claim 1, wherein in the partially-opened position, a maximum opening angle between the first and second housing portions of the second connector is between 6.5° and 7°, inclusive.

7. The system of claim 1, wherein the stop opening has a dumbbell-shape.

8. The system of claim 1, wherein the stop opening has an hourglass-shape.

9. A connector attached to an electrical cable in a patient treatment system for delivering therapy to a patient, the connector comprising:
   a first housing portion having a stop opening extending therethrough, and a longtiduinally extending slot that is configured to slidably receive a portion of a spinal cord stimulation lead; and
   a second housing portion having a stop element received in the stop opening and moveable within the stop opening, and a plurality of connector contacts positioned to electrically contact a plurality of connection contacts of the lead, and a plurality of snap-fit latches to securely carry a surface having the second connector contacts,
   wherein the first and second housing portions are pivotably connected to each other to move between a partially-opened position, in which the stop element is in a first location within the stop opening, and a closed position in which the stop element is in a second location within the stop opening.

10. The system of claim 9, wherein in the partially-opened position, the connection contacts of the lead are disengaged from the connector contacts.

11. The system of claim 9, wherein in the closed position, the connection contacts of the lead are engaged with the connector contacts.

12. The system of claim 9, wherein in the partially-opened position, a maximum opening angle between the first and second housing portions of the connector is between 3° and 15°, inclusive.

13. The system of claim 9, wherein in the partially-opened position, a maximum opening angle between the first and second housing portions of the connector is between 5° and 8°, inclusive.

14. The system of claim 9, wherein in the partially-opened position, a maximum opening angle between the first and second housing portions of the connector is between 6.5° and 7°, inclusive.

15. The system of claim 9, wherein the stop opening has a dumbbell-shape.

16. The system of claim 9, wherein the stop opening has an hourglass-shape.

17. A connector for an electrical cable in a spinal cord stimulation system, the connector comprising:
   a first housing having an elongated stop opening extending therethrough; and
   a second housing having
      a stop element received in the elongated stop opening and moveable within the stop opening,
      a plurality of connector contacts positioned to electrically contact connection contacts of a lead, and
      a plurality of snap-fit latches positioned to secure a support member carrying the connector contacts;
   wherein the first and second housings are movable relative to each other between a partially-opened position, in which the stop element is in a first location within the elongated stop opening, and a closed position in which the stop element is in a second location within the elongated stop opening.

18. The system of claim 17, wherein in the partially-opened position, the connection contacts of the lead are disengaged from the connector contacts.

19. The system of claim 17, wherein in the closed position, the connection contacts of the lead are engaged with the connector contacts.

20. The system of claim 17, wherein in the partially-opened position, a maximum opening angle between the first and second housing portions of the connector is between 3° and 15°, inclusive.

21. The system of claim 17, wherein in the partially-opened position, a maximum opening angle between the first and second housing portions of the connector is between 5° and 8°, inclusive.

22. The system of claim 17, wherein in the partially-opened position, a maximum opening angle between the first and second housing portions of the connector is between 6.5° and 7°, inclusive.

23. The system of claim 17, wherein the elongated stop opening has a dumbbell-shape.

24. The system of claim 17, wherein the elongated stop opening has an hourglass-shape.

* * * * *